United States Patent
Boosfeld et al.

(10) Patent No.: US 6,338,736 B1
(45) Date of Patent: *Jan. 15, 2002

(54) STRENGTHENED IMPLANT FOR BODILY DUCTS

(75) Inventors: Christoph Boosfeld, Aachen; Franz Freudenthal, Bonn, both of (DE)

(73) Assignee: pfm Produkte für die Medizin Aktiengesellschaft, Köln (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,398

(22) PCT Filed: May 6, 1997

(86) PCT No.: PCT/EP97/02300

§ 371 Date: Jan. 22, 1999

§ 102(e) Date: Jan. 22, 1999

(87) PCT Pub. No.: WO97/42881

PCT Pub. Date: Nov. 20, 1997

(30) Foreign Application Priority Data

May 14, 1996 (DE) .......................................... 196 21 157
Feb. 5, 1997 (DE) .......................................... 197 04 269

(51) Int. Cl.[7] ........................................... A61M 29/00
(52) U.S. Cl. ..................... 606/191; 606/194; 623/1.22
(58) Field of Search ...................... 606/191, 192–200; 623/1, 12

(56) References Cited

U.S. PATENT DOCUMENTS

| | | |
|---|---|---|
| 4,994,069 A | 2/1991 | Ritchart et al. |
| 5,382,259 A | 1/1995 | Phelps et al. |
| 5,522,822 A | 6/1996 | Phelps et al. |
| 5,536,274 A * | 7/1996 | Neuss .......................... 623/1 |

FOREIGN PATENT DOCUMENTS

| | | |
|---|---|---|
| DE | 32 03 410 A1 | 11/1982 |
| DE | 158 084 | 12/1982 |
| EP | 0 571 422 B1 | 8/1994 |
| EP | 0 747 012 A1 | 12/1996 |
| WO | WO92/14408 | 9/1992 |
| WO | WO95/25480 | 9/1995 |

OTHER PUBLICATIONS

World Intellectual Property Organization "International Search Report from International Application Published Under the Patent Cooperation Treaty, International Publication No. WO 97/42881," p. 3, (Nov. 20, 1997).

World Intellectual Property Organization, "International Preliminary Examination Report from International Application Published Under the Patent Cooperation Treaty, International Publication No. WO 97/42881," p. 5, (Nov. 20, 1997).

* cited by examiner

Primary Examiner—David O. Reip
(74) Attorney, Agent, or Firm—Paul A. Beck & Associates (57) ABSTRACT

An implant is provided for closing passages in organs and defects. The implant has a primary structure, e.g. coil, of a resilient material, where the implant in an operational state, forms a secondary structure, e.g. coil, of greater diameter than that of the primary coil. The implant can be converted by a guide element from the shape of the secondary coil into a transporting state in which the implant adopts an elongate shape, and the implant once again assumes the operational state by removal of the guide element. In order to improve the success of treatment, it is proposed, for achieving a better securing of the implant in a larger passage of an organ, that the primary coil has areas of different transverse spring rate along its longitudinal extent. A set is furthermore proposed with an implant according to the invention, and a device for applying such an implant with a guide element.

36 Claims, 8 Drawing Sheets

STRENGTHENED IMPLANT FOR BODILY DUCTS

BACKGROUND OF THE INVENTION

1. Field of the Invention

The present invention relates to an implant for closing passages in organs, comprising a primary coil of a resilient material, where the implant, in an operational state, forms a secondary structure of greater diameter compared to the primary coil, where the implant can be converted by a guide element from the shape of the secondary structure into a transporting state in which the implant adopts an elongate shape, and the implant, after separation from the guide element, once again assumes the operational state, and also a set containing the implant and an insertion device for the implant.

2. Description of the Currently Available Technology

For many years now, in invasive surgery, such implants for closing vessels have been implanted by means of catheters. DD-A-158,084 discloses a wire coil for intraarterial and intravenous closure of blood vessels. Here, a wire coil is shaped to give a helical spring body such that, on application of an external force, it can be deformed elastically to a straight wire coil and, after the force is released, assumes a knot-shaped configuration.

EP-B1-0,571,422 describes various forms of implants and a device of the type mentioned in the introduction. Accordingly, the primary coil can be made from a suitable wire material or an elastic polymeric tube. A particular embodiment of the implants of the type described at the outset is proposed in EP-B1-0,571,422 in which the proximal end of such an implant is designed in a specific way so as to solve, with an appropriate applicator, the problem of, on the one hand, being able to push the primary coil off from a guide wire and, on the other hand, maintaining a sufficiently secure connection between primary coil and guide wire when the primary coil has almost completely formed the secondary coil. This is of particular importance in order to correct possible dislocations caused by the opening-out of the secondary coil, and, if need be, to pull the primary coil back at least partially onto the guide wire 10 again. At the same time, however, the connection between primary coil and guide wire must be designed such that the primary coil can also be finally pushed off from the guide wire without excessive forces being required.

U.S. Pat. No. 5,382,259 discloses implants for closing passages in organs, which implants have, at both ends, short coil pieces which are connected to one another via a cylindrical fibrous fabric or mesh. In one embodiment, the two coil pieces located at the ends are additionally coupled to one another via a wire. This wire can consist of a memory metal such as, for example, the alloy nitinol. It is in this case described as an advantage if the wire has a secondary structure which forms after implantation. Thus, on account of the soft fabric or mesh which adapts to the structure of the wire, a second configuration of the implant with an increased diameter is formed. The configuration of the coil pieces located at the ends thereby remains unaltered.

In a further embodiment disclosed in U.S. Pat. No. 5,382,259, a continuous wire coil is enclosed by a fabric of silk or by a synthetic fibre in order to form a thrombotically active surface. This fabric has no supporting function whatsoever.

A problem of the known implants is, however, the closure of larger openings. When the conventional primary coils are used to form larger secondary coils, there is the problem that the forces sufficient to hold the implant securely in the desired position are no longer available in the outer turns of the secondary coil. This problem can be avoided by increasing the rigidity of the primary coil, for example by using stronger wire. However, the result of this is that, in the centre of the secondary coil, it is no longer possible to have such small radii of the secondary coil as when using softer primary coils. This has the effect that a fairly large hole remains in the centre of such a secondary coil. Since in practice this hole can only be closed by thrombosis, going beyond certain minimum values means that a tight closure of the vessel can no longer be achieved. Thus, implants with complex secondary structures in particular, in which both small and large radii of curvature are formed, and which thereby ensure a particularly tight closure, cannot be used for closing larger openings.

Also in the case of the implants disclosed in U.S. Pat. No. 5,382,259 and described above, the closure of larger openings leads to problems. Said specification discloses a fabric which encloses the wire, has no supporting functions whatsoever, and serves only to create a thrombotic surface. The dimensional stability of the secondary configuration of the implant has to be provided solely by the central wire. If the dimensional stability sufficient for secure closure of large openings is to be achieved in the outer areas too, then the wire must have very great rigidity, and this makes it very difficult to stretch the wire out for the purpose of inserting the implant into a catheter, or indeed makes this impossible. For this reason, these implants are also only suitable for closing small openings. In addition, U.S. Pat. No. 5,382,259 discloses only very simple secondary structures with large radii, and in particular without any great differences in the radii. This results in a very open structure whose closure can be achieved only by virtue of the thrombotic action of the fabric.

SUMMARY OF THE INVENTION

The invention is therefore based on the object to provide an implant of the type mentioned at the outset, in particular with a complex secondary structure with different radii of curvature, and with which implant it is possible to reliably close even larger vessel defects, for example in the central circulatory system, where there is a strong blood flow and also a high blood pressure. A further object of the present invention is to provide a suitably adapted device for application of such an implant.

This object is achieved by means of an implant of the type mentioned at the outset, which implant is characterized in that the primary coil has areas of different bending rigidity along its longitudinal extent. In the case of an implant having a secondary structure with different radii of curvature, it is particularly advantageous if the primary coil has, in the areas of large radii of curvature of the secondary structure, a greater transverse spring rate than in the areas of smaller radii of curvature of the secondary structure.

With such a primary coil, it is possible for very complex secondary structures having different radii of curvature to be constructed. The areas of lower transverse spring rate are in this case formed into turns with small radii, and the areas of greater transverse spring rate are formed into turns with large radii. This ensures that in areas of small radii of the turns of the secondary structure, the primary coil is sufficiently soft to enable the secondary structure to be simply stretched out again, for example for inserting the implant into a catheter, and at the same time, in areas of greater radii of the turns of the secondary structure, the primary coil is sufficiently rigid to reliably guarantee the dimensional stability necessary for tight closure of a vessel defect, even in the case of large openings and the associated large radii of curvature of the secondary structure.

In accordance with the present invention, secondary structures can be developed by twisting the primary coil, which assumes the shape of a cylinder, a cone, a double cone with greater radii at the ends, a double cone with different radii at the ends, a cylinder in which turns of the secondary structure with different radii alternate with each other, two spirals connected by a cylindrical section, a double rosette, a double cone, where the turns of the second cone are wound onto the turns of the first cone, or assumes the shape of a plurality of eight shapes. By appropriate adjustment of the bending rigidity in different areas of the primary coil, cone or spiral structures can be constructed in which the radii of the turns increase, in a conical or helical shape, from a minimum radius, of the order of size of the cross-sectional radius of the primary coil, up to 15 mm. Optimal sealing, even of large defect openings, can be achieved in this way. With the implants according to the invention, secondary structures can be constructed which are in themselves so compact that they almost have the character of a membrane. Although, in accordance with the present invention, the additional sealing by means of thrombotically active structures may be desirable, it is nevertheless no longer necessary for secure sealing, in contrast to the prior art, as represented, for example, by U.S. Pat. No. 5,382,259.

It is in this case particularly advantageous if the primary coil contains at least one additional body by means of which the different transverse spring rate is produced.

A particularly preferred embodiment of the present invention is characterized in that the primary coil includes, on at least one part of its length, at least one further primary coil. By introducing a further primary coil of this kind into the original primary coil, the rigidity and the restoring forces of the primary coil can be deliberately modified in certain desired areas in an extremely simple way. Depending on the design of the secondary coil, the further primary coil can be accordingly arranged inside the original primary coil. It is particularly advantageous if the further primary coil is screwed into the original primary coil.

In an especially expedient embodiment for simple secondary coils, such an implant is characterized in that at least one end section of the primary coil includes, on at least one part of its length, at least one further primary coil. It is thus possible to obtain, in an extremely simple way, a secondary coil which on the one hand has very narrow turns, and consequently the smallest possible residual hole, and which on the other hand has high restoring and clamping forces at its other end, even with large radii. This ensures, on the one hand, that the vessel can be closed completely with the greatest possible certainty, and, on the other hand, that the implant also sits sufficiently securely in place.

Particularly for use as secondary coils in the form of double discs or double cones, it is expedient if both end sections of the primary coil each include, on at least one part of their lengths, at least one further primary coil. Such double-sided secondary coils form the central turns of the secondary coil approximately at half the length of the primary coil. By means of the arrangement according to the invention, it is once again possible, also in the case of double-sided secondary coils, to allow very small secondary coil radii in the area of the smallest turns, i.e. approximately at half the length of the primary coil, and, on the other hand, to provide sufficiently high spring forces in the outer turns of the two secondary coil parts, on both sides of the vessel wall to be closed. The previously described advantages of an implant according to the invention can thus also be employed particularly well in the case of double-sided secondary coils.

The effect which can be achieved by means of the invention can be further enhanced if at least one end section of the primary coil includes, on at least one part of the length of the further primary coil, at least one additional primary coil, i.e. if the further primary coil is additionally provided on one part with an additional primary coil, so that the rigidity or spring rate of the primary coil increases still further in this area. For use in double-sided secondary coils, it is accordingly expedient if both end sections of the primary coil each include, on at least one part of the lengths of the further primary coils, at least one additional primary coil.

With regard to a more secure fitting of the implant upon application, but still with easier intentional removability from the guide element, it is particularly expedient if the turns of the primary coil or of the primary coils are stretched out in the area of a proximal end section.

In one embodiment which is particularly expedient from the point of view of production engineering, the primary coil or the primary coils has/have, in the area of the proximal end section, a noncircular cross-section, in particular an approximately polygonal cross-section, particularly preferably an approximately triangular cross-section, or a tapered circular cross-section. The tapered circular cross-section can be obtained by screwing into the original primary coil a further primary coil of reduced internal diameter, which advantageously corresponds to the diameter of the core wire used as insertion aid.

In a particularly preferred embodiment, the further primary coils and the additional primary coils have approximately the same external diameter as the primary coil. As a result, an exact guide is also achieved within a catheter with which such an implant is applied.

For the necessary application of the implant via a catheter, it is particularly expedient if the further primary coils and the additional primary coils are wound between the turns of the primary coils.

In an alternative embodiment of the implant according to the invention, the primary coil can have, within its lumen, a core having areas of different bending rigidity, at least relative to a reference plane, along its longitudinal extent.

In accordance with a preferred embodiment of the present invention, the core is made up of a plurality of wires, the number of wires in areas of greater bending rigidity of the primary coil being greater than in areas of lower bending rigidity. With this embodiment, a secondary structure in the form of a double cone can be obtained as follows. Thus, for example, it is possible to use, for the core, one individual wire which is doubled back in the two end areas of the primary coil, while the wire in the middle area of the primary coil, which in the secondary structure is formed into turns with small radii of curvature, is present only as individual wire. Alternatively, a different number of wires of different length can be introduced into the primary coil, according to the desired pattern of bending rigidity of the primary coil. Since, in the secondary forms described above, the primary coil must have the greatest bending rigidity at its ends, the number of the individual wires is greatest at the end areas, in accordance with the embodiment described above. The individual wires can be connected to the primary coil by simple means, for example by welding at the ends, so that slippage of the individual wires and thus a change in the pattern of bending rigidity of the primary coil is avoided.

In a particularly preferred embodiment, the core contains one individual wire or a number of wires remaining the same over the entire length of the primary coil, where the wire or the wires has/have a changing diameter, with a greater diameter in areas of greater bending rigidity, and a smaller diameter in areas of lower bending rigidity. In this embodiment, the desired pattern of the bending rigidity in the primary coil can be achieved simply by changing the cross-section of the wire. In this case it is particularly advantageous if only one individual wire having an appropriately adapted cross-section pattern is used. This has the additional advantage that the primary coil can be produced in a simple manner.

In an alternative embodiment, the core likewise contains one individual wire or a number of wires remaining the same over the entire length of the primary coil, where the wire or the wires in this embodiment has/have a circular cross-sectional surface area in the area of lower bending rigidity, and a polygonal cross-sectional surface area in areas of greater bending rigidity. It is in this case advantageous if the diameter of the inner circle of the polygonal cross-sectional surface area corresponds at least to the diameter of the circular cross-sectional surface area in the areas of lower bending rigidity. In this embodiment too it is preferable to use only one individual wire for the core. Here, the polygonal cross-sectional surface area is preferably triangular or rectangular, in particular square.

In a further embodiment of the implant according to the invention, the core of the primary coil contains one or more flat wires. In this case the flat wire or the flat wires is/are arranged inside the primary coil in such a way that, upon formation of the secondary structure of the implant, the flat wire or the flat wires, in areas of the secondary structure having small radii of curvature, is/are bent out from the plane which extends parallel to the broad side of the flat wire, and, in areas of the secondary structure having by comparison greater radii of curvature, is/are bent within this plane. In this embodiment, a different bending rigidity relative to a reference plane of the primary coil can be achieved in a particularly simple way by twisting a flat wire which is used as core for the primary coil. This embodiment is particularly advantageous since a simple flat wire with no change in its cross-sectional surface area can be used to produce the primary coil according to the invention, and the changing bending rigidity relative and to a fixed reference surface can be achieved by simple twisting of the flat wire. It need simply be observed here that upon formation of the secondary structure, the primary coil is wound in accordance with the instructions described above.

It is particularly advantageous here if the twisting of the flat wire takes place upon production of the secondary structure of the implant. For this purpose, the primary coil is wound so that in areas of large radii of curvature of the secondary structure the primary coil is bent within the plane parallel to the broad side of the flat wire and, in areas of small radii of curvature, is bent perpendicular thereto. This has in particular the advantage that the implant in the stretched state is very soft and can be manipulated easily, for example inside the insertion catheter, and yet in the implanted state inside the defect opening is nevertheless arranged in such a way that in the areas of large radii of curvature of the secondary structure, the flat wire extends so that the blood impinges on the implant parallel to the broad side of the flat wire, as a result of which optimal transverse spring rate for the implant is obtained in the critical areas.

The twisted configuration of the flat wire inside the primary coil can be fixed by securely connecting the primary coil to the flat wire at both ends. As will be discussed later, however, this is not necessary in a preferred production method in which a memory alloy is used both for the core and also for the primary coil, and the secondary structure is designed jointly for core and primary coil. In such a production method, the clamping forces which occur between core and primary coil are so great that no relative movement takes place between core and primary coil.

In a further embodiment of the present invention, the core contains, within the primary coil, a braid which has areas with a different number of windings of the individual wires per unit of length of the braid. In the areas of the braid with a greater number of windings of the individual wires per unit of length of the braid, i.e. in areas of the braid which are more strongly twisted, the bending rigidity of the braid is lower than in areas with a smaller number of windings of the individual wires per unit of length of the braid, i.e. in areas which are less strongly twisted. Thus, a suitable pattern of bending rigidity can be obtained simply by differential twisting of the braid along its length.

In all the embodiments described above, it is preferable if a resilient material is likewise used for the core, it being particularly advantageous if both the primary coil and also the core consist of a memory alloy such as, for example, nitinol. Since in at least some of the embodiments described above the bending rigidity of the primary coil, at least relative to a reference plane, depends on the orientation of the core relative to the primary coil, it is preferable to connect the primary coil and the core to one another at least at one end, preferably at the distal end of the implant, in order to prevent a relative movement of core and primary coil. This can be done in any way known to the skilled expert, for example by welding. In this case it is particularly advantageous if a spherical cap is formed at the distal end when welding together the two constituent parts, so that a blunt end is obtained, in order to prevent injury to the passages in the organs during insertion of the implant.

The implant also has, at the proximal end, a positioning device via which the implant can be brought safely to the predetermined location and can be separated from the insertion device. The positioning device can be arranged either on the primary coil or the core. The positioning device is preferably interlocking, in particular an eyelet.

In embodiments of the implant in which the core contains a doubled-back wire, the resulting loop can protrude at the proximal end from the primary coil, as a result of which an eyelet is formed which can function as positioning device.

The implants according to the invention can be produced in different ways. In one embodiment, the primary coil, consisting of a primary wire of specific strength, and the core are produced separately from one another in accordance with the embodiments described above, and the core is subsequently introduced into the primary coil. The primary wire, which is used for producing the primary coil, in this case preferably has a diameter of 0.05 to 0.35 mm. The internal diameter of the primary coil is in this case adapted to 6 the maximum diameter of the core and lies in the range from 0.15 to 0.60 mm.

Alternatively, the core in accordance with the embodiments described above can be produced first, and the primary coil can then be produced by means of winding around the core.

A common feature of both embodiments is then that the composite consisting of core and primary coil is reshaped from the elongate form into the respective desired secondary structure. Both primary coil and also core are preferably formed from a resilient material with memory effect, for example the memory alloy nitinol. In such a case, the secondary structure of the implant can be imposed by heat treatment in a temperature range from 300 to 500 EC and subsequent quenching. In this way, in the unstressed state, the implant assumes the desired secondary structure, as discussed above for example, and can be stretched out once again, for example by insertion into a catheter. Then, after leaving the catheter, the implant changes back to the secondary structure.

In one embodiment, core and primary coil can be connected to each other by conventional methods, such as, for example, welding. In this case, however, it must be noted that the memory effect, as described above, is not annulled by this procedure. As has already been described above, however, a connection of core and primary coil is not absolutely necessary since on account of the clamping forces between core and primary coil in an implant that has been produced as described above, no relative movement takes place between core and primary coil.

In a particularly preferred embodiment of the implant according to the invention, the secondary structure can assume the shape of a double cone by winding the primary coil, in which double cone the turns of the second cone are wound onto the turns of the first cone. In the forms of implants hitherto known, as are described in EP-A-0 571 422, for example cone, double cone or spiral shape, there is the risk of the implant itself winding up because of movements or impinging blood and thus being displaced. In the preferred secondary structure described above, this risk is greatly reduced, since the individual turns which make up the cone structure can no longer be so easily pulled open, since the turns of the second cone lie crosswise to the turns of the first cone, and slipping is thereby prevented. In the case of smaller organ defects which are to be closed, this implant can thus also be used to advantage without variable rigidity of the primary coil.

The present invention furthermore relates to a set which includes an implant according to the invention, as well as an insertion device with an insertion catheter, and an insertion element which can be connected releasably to the implant and is movable inside the insertion catheter.

In the embodiments of the implant with an open lumen, the set according to the invention includes a guide element which, in the area of its distal end, has a widened portion on one part of its length, in an axis transverse to the longitudinal axis of the guide element. The use properties of such a guide element with an implant according to the invention are improved in this way, since the frictional connection between primary coil and guide element is improved without appreciably increasing the friction upon the intended detachment of the primary coil from the guide element. This is particularly the case when the guide element has, in the area of its distal end, at least one further widened portion on one part of its length, in an axis transverse to the longitudinal axis of the guide element and approximately transverse to the widened portion. In this case, it has proven expedient in practice if the widened portion amounts to about 1.15 times the diameter of the guide element outside the areas of the widened portions.

In the embodiments of the implant with a core, the guide element, in a simple design of the insertion device, is a positioning wire which has a hook which engages in the positioning device of the implant, for example in the eyelet.

In addition, the insertion device also has the necessary operating elements for moving catheter and guide wire in relation to each other and within the body of the patient or animal.

Before the intervention, the positioning wire is guided through the catheter so that the distal end of the positioning wire protrudes from the distal end of the catheter. The positioning wire is then connected to the implant, for example by engagement of the hook in the positioning device of the implant, for example the eyelet. Thereafter, to establish a transport state, the positioning wire and the connected implant are drawn back into the catheter, as a result of which the secondary structure of the implant is converted into the stretched out transport form. The set can advantageously be packaged sterile and made available to the operator in this transport form.

In the actual implantation procedure, the catheter, including implant and positioning wire, is advanced by conventional means as far as the location inside the body where the implant is to be fitted. The correct positioning can be verified by radiography. For improved radiographic identification, the implant can have additional radiopaque markings.

For positioning the implant, the positioning wire is advanced through the inside of the catheter, as a result of which the implant is pushed out of the catheter and thus, when completely released from the catheter, once again assumes its secondary structure. The implant is thereafter separated from the positioning wire.

In a preferred embodiment, the positioning wire has, at the distal end, a releasable eyelet which can be formed, for example, by partial doubling-back of the positioning wire inside the catheter, and which engages in the positioning device of the implant, for example in the eyelet. This embodiment has the advantage that after the implant has been released from the catheter, there is still a secure connection between implant and positioning wire, so that in the event of a possible incorrect positioning of the implant, the latter can be pulled back into the catheter again and the positioning can be corrected. For final detachment of the implant, the releasable eyelet on the positioning wire is then opened, for example by advancing the positioning wire through the inside of the catheter until the doubled-back part of the positioning wire springs open. By pulling on one end of the positioning wire, the latter can then be pulled out completely from the eyelet of the implant, as a result of which the implant is finally detached.

In a particularly preferred embodiment, the positioning wire has a loop which is interlaced with the eyelet of the implant and is secured against separation from the eyelet by means of a locking wire. This embodiment likewise has the advantage that the implant, in the event of possible incorrect positioning, can be pulled back into the catheter, although the detachment of the implant is considerably easier in this case since, while holding the positioning wire secure, only the locking wire has to be pulled back into the catheter until the loop of the positioning wire and the eyelet of the implant are separated from one another. This permits a simple and secure positioning of the implant.

BRIEF DESCRIPTION OF THE DRAWINGS

The invention will be explained in greater detail hereinbelow on the basis of illustrative embodiments which are represented in the drawings, in which.

DESCRIPTION OF THE PREFERRED EMBODIMENTS

Figure 1:
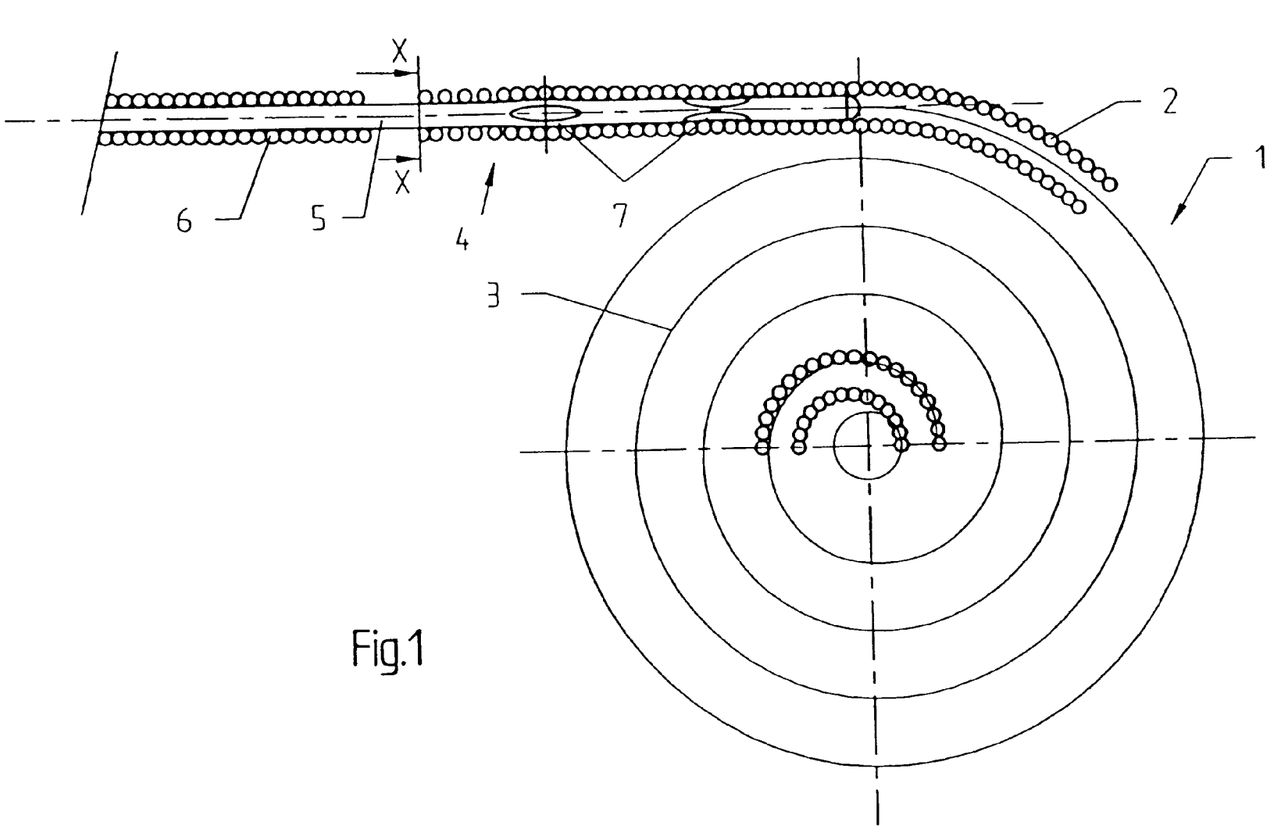
FIG. 1 shows an implant according to the invention which has been substantially pushed down from a guide element of an application device according to the invention.

FIG. 1 shows an implant 1 according to the invention, with a primary structure or coil 2. The greatest part of the primary coil 2 has already adopted the form of the secondary coil 3. A proximal end section 4 of the primary coil 2 is still arranged on a guide wire 5, which here serves as guide element for a device for applying the implant. For the purpose of improved clarity, the representation is shown in the plane of the guide wire 5 in cross-section and partly stylized.

The device for applying an implant according to the invention also includes, in addition to the guide wire 5, a pusher coil 6 with which the primary coil 2 can be pushed from the guide wire 5. Outside the area which is represented, the device also includes, as outer sheath, a catheter through which the implant is introduced into the human or animal body. Outside the body, the device also has the necessary operating elements for moving the catheter, pusher coil 6 and guide wire 5 in relation to one another and within the body of the patient or animal.

As can clearly be seen, the guide wire 5 in this case has, in the area of its distal end, two widened portions 7 which are each arranged approximately transverse to one another and to the longitudinal axis of the guide wire 5. The widened portions 7 are produced simply by appropriate forging of the guide wire 5. Such a guide wire 5 is expediently produced from a highly elastic nickel/titanium alloy, so as to be able to introduce the implant into angled vessels too.

The primary coil 2 is preferably wound from metal wire having exceptional spring characteristics. So that the primary coil 2 from the guide wire 5 also assumes complicated forms of the secondary coil 3, such as, for example, the double cone represented in FIG. 5, highly elastic spring steels are suitable in particular as material for the primary coil 2. By appropriate pre-forming of the secondary coil 3 and by subjecting the implant to a defined heat treatment, the desired form of the secondary coil 3 can thus be obtained after detachment of the primary coil 2 from the guide wire 5. Suitable materials are, for example, corrosion-resistant spring steels or memory alloys.

The primary coil 2 can also be designed as a thin tube, however, and can be made from a suitable thermoplastic. Suitable plastics are, for example, polyurethane homopolymers or copolymers, polyolefin copolymers or silicone elastomers. For certain medical applications, however, absorbable polymers may also be suitable, such as aliphatic polyesters, for example polydioxanone.

Figure 2:
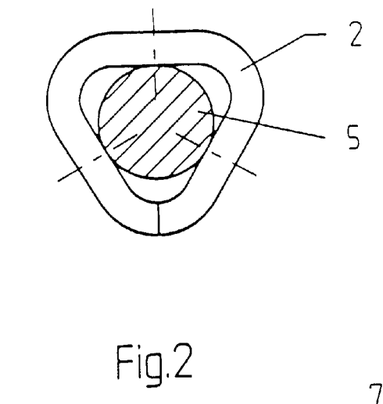
FIG. 2 shows a cross-section along the line X—X in FIG. 1.

In the cross-section in FIG. 2 along the line X—X from FIG. 1, and in FIG. 1, it will be seen that the primary coil 2 is stretched out at its proximal end over a length of approximately 4 to 5 turns, and the stretched out turns are pressed to give an approximately triangular cross-section. This pressing reduces the internal diameter of this area of the primary coil 2. Reducing the internal diameter ensures that the primary coil 2 cannot slip unintentionally from the guide wire 5, as will be explained in greater detail hereinafter with reference to FIG. 3. The crosswise arrangement of the widened portions 7 (see FIG. 1) ensures that the primary coil 2 is at all times subject to a sufficient clamping force, so that unintentional slipping of the primary coil 2 from the guide wire 5 is in practice ruled out.

Figure 2A:
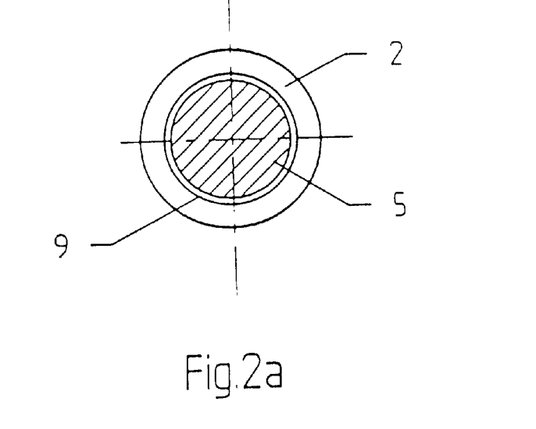
FIG. 2a shows a cross-section of an alternative embodiment at a location comparable to FIG. 2.

Alternatively, as can be seen from FIG. 2a, the reduction in the internal diameter of the primary coil 2 can be achieved by incorporation, for example screwing-in, of a second or further primary coil 9 with reduced internal diameter. In this case, the internal diameter of the further primary coil 9 essentially corresponds to the basic external diameter of the positioning wire 5. Using the positioning wire 5 represented in FIG. 1 or FIG. 3 with widened portions 7 thus ensures, independently of the relative position of primary coil 2 and guide wire 5 to one another, that the primary coil 2 is subject to a sufficient clamping force so that unintentional slipping of the primary coil 2 from the guide wire is reliably prevented.

The particular effect of stretching out the last 4 to 5 proximal turns of the primary coil 2 is that, when detachment of the primary coil 2 from the guide wire 5 is desired, the pusher coil 6 presses these stretched-out end turns of the primary coil 2 together, as a result of which at the same time the internal diameter is increased and, thus, the friction when pushing the primary coil over the widened portions 7 is considerably reduced. Only slight forces are therefore necessary for the final detachment of the primary coil 2 from the guide wire 5, as a result of which incorrect positioning and slipping of the implant are to a very great extent avoided. Nevertheless, this arrangement affords a secure holding of the primary coil 2 on the guide wire 5 in the other operating states.

Figure 3:
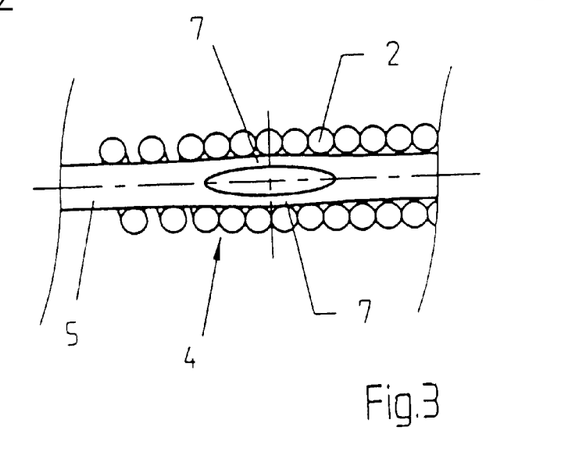
FIG. 3 shows an enlarged section of an arrangement according to FIG. 1.

In FIG. 3, the widened portion 7, which is generated by forging the guide wire 5, is represented on an enlarged scale. As suitable for forming the necessary clamping force, trials have shown that it is expedient if the guide wire 5, in the area of the widened portions 7, has approximately 15% greater dimensions than the diameter of the guide wire 5 outside the areas of the widened portions.

Figure 4:
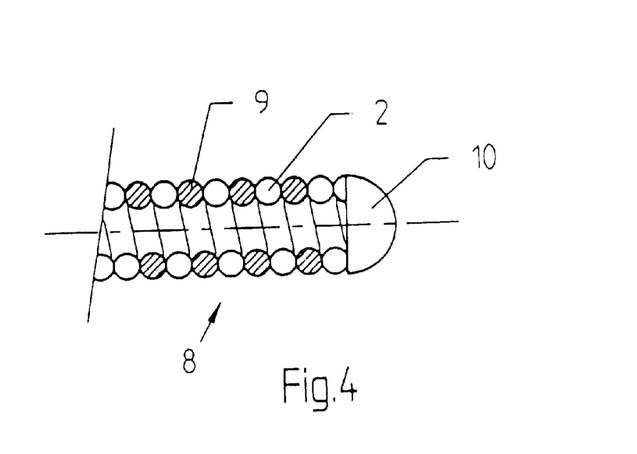
FIG. 4 shows a distal end of a primary coil of an implant according to the invention.

FIG. 4 shows a further primary coil 9 which is wound into a distal end section 8 of the primary coil 2. The further primary coil 9 includes three windings. The distal end of the primary coil 2 is covered by a welded-on spherical cap 10 in order to prevent injuries and punctures of vessel walls in the patient or animal during application of the implant 1. The spherical cap 10 can at the same time also be welded to the further primary coil 9 and, if appropriate, to additional primary coils, this in each case ensuring a secure fit of the further primary coil 9 and, if appropriate, of the additional primary coils inside the distal end section 8 of the primary coil 2, even under unfavourable conditions.

It will be seen from FIG. 4 that the effect according to the invention can be enhanced if an additional primary coil, for example over 5 windings, is additionally introduced (not shown), for example in addition to a further primary coil 9 which extends over about 25 windings in the primary coil 2. To realize extreme spring characteristics, a plurality of additional primary coils can also be used accordingly.

Figure 5:
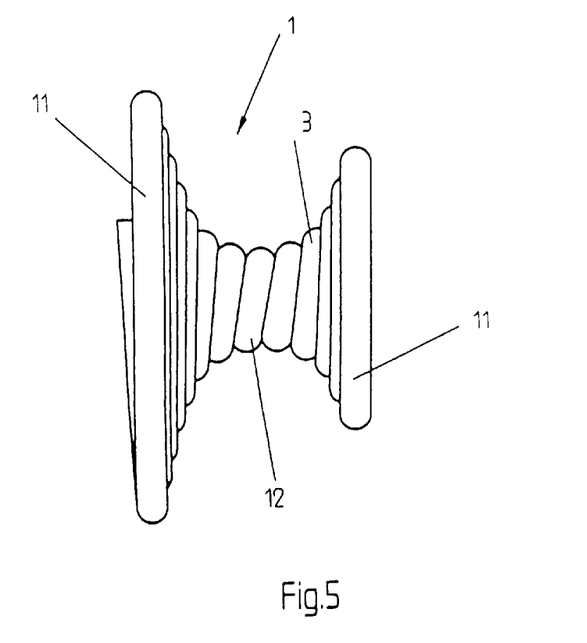
FIG. 5 shows a double-sided secondary coil of an implant according to the invention, in the form of a double cone, in a side view.

FIG. 5 shows an implant 1 according to the invention which, in its secondary structure 3, assumes the form of a double cone. In this form, there are areas 11 with large radii of curvature and areas 12 with small radii of curvature of the secondary structure 3.

Figure 6:
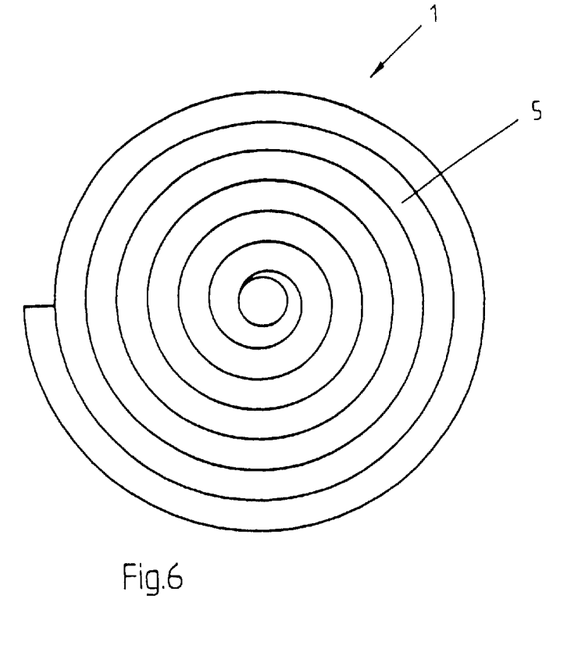
FIG. 6 shows a double-sided secondary coil of an implant according to the invention, in the form of a double disc, in a front view.
Figure 7:
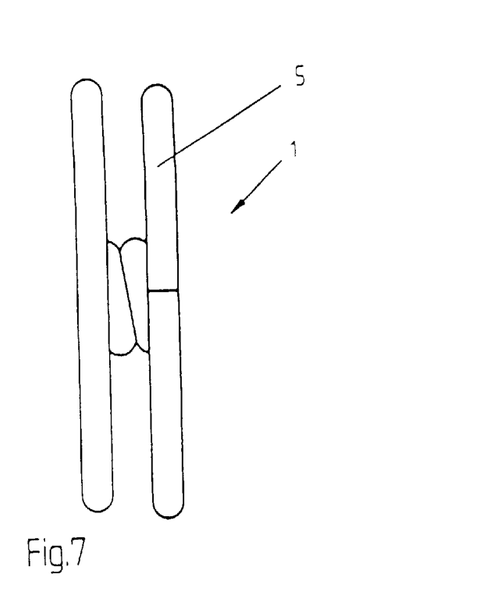
FIG. 7 shows the secondary coil from FIG. 6 in a side view.

FIGS. 6 and 7 show particularly clearly how the invention can be used in the case of doubled secondary coils 30 with extreme cross-section variations. With the aid of an implant 1 according to the invention, cross-sectional ratios of residual hole diameter to external diameter of the secondary coil 3 of the order of size of 1:15 can be achieved.

Figure 8:
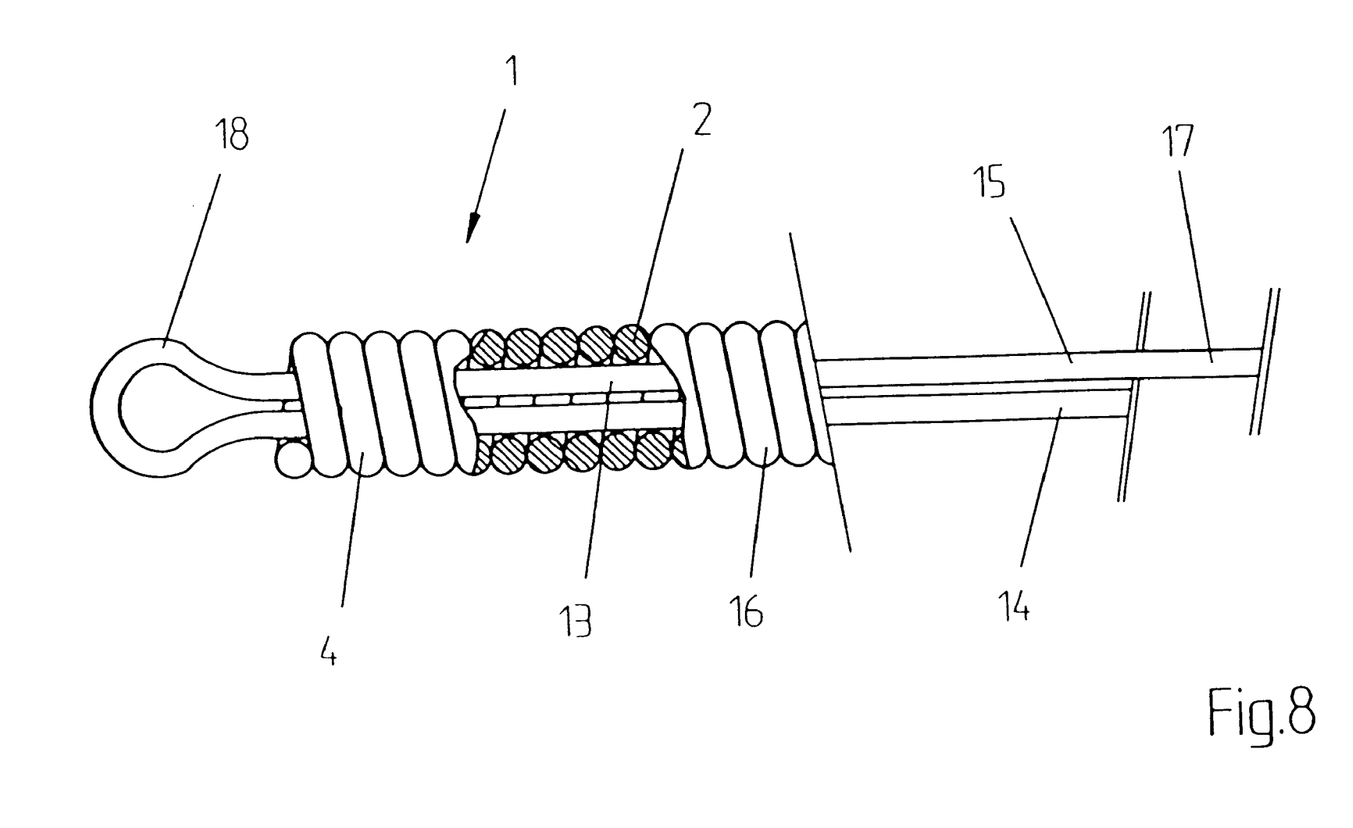
FIG. 8 shows a side view of a further embodiment of the implant according to the invention, with a core having a variable number of individual wires along its longitudinal extent, in which figure, for the purpose of improved clarity, the primary coil is in part shown in cross-section and is in part omitted.

FIG. 8 shows diagrammatically the proximal end section 4 of an implant 1 according to the invention, in which a core 13 is arranged in the lumen of the primary coil 2. In this embodiment, the core 13 consists of a wire which is doubled back in the proximal end section 4 of the implant 1. Where 2 individual wires 14, 15 lie next to one another, this creates an area 16 of higher bending rigidity, which, in a secondary structure 3 as represented in FIG. 5, is assigned to an area 11 of greater radius of curvature, and in the region where the core 13 is formed by only one wire 15, this creates an area of lower bending rigidity, which is assigned to an area 12 of smaller radius of curvature of the secondary structure 3. The doubling back of the wire 15 creates an eyelet 18 which serves as positioning device. To establish a secondary structure 3 in the form of a double cone, as is represented in FIG. 5, it is expedient if the core 13 is likewise doubled back in the distal end section, which is not shown in FIG. 8. This provides the primary coil 2 with end sections of higher transverse spring rate, which are assigned to the areas of large radii of curvature of the secondary structure, and a central area of lower transverse spring rate, which is assigned to the area of smaller radius of curvature of the secondary structure. It is furthermore advantageous if either the primary coil or the core is made from a memory metal.

Figure 9:
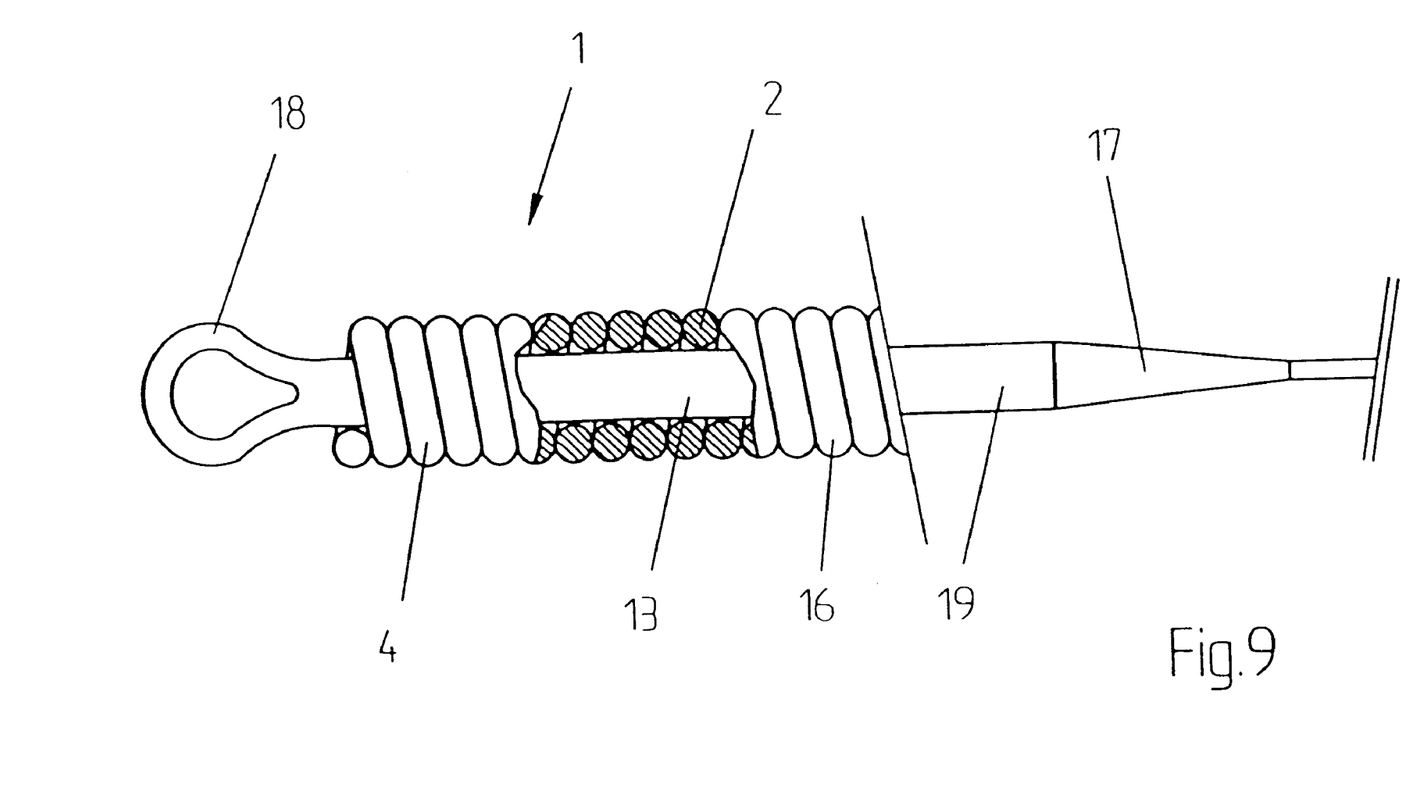
FIG. 9 shows a side view of a further embodiment of the implant according to the invention, with a core having a variable cross-section along its longitudinal extent, in which figure, for the purpose of improved clarity, the primary coil is in part shown in cross-section and is in part omitted.

In the embodiment of the implant 1 according to the invention represented in FIG. 9, the areas of different transverse spring rate are generated by a conically extending wire 19. Analogous to the embodiment in accordance with FIG. 8, the wire 19 has a greater cross-section in the end areas than it does in the central area. The proximal end of the wire 19 is likewise designed in the form of an eyelet 18 which functions as positioning device.

Figure 10:
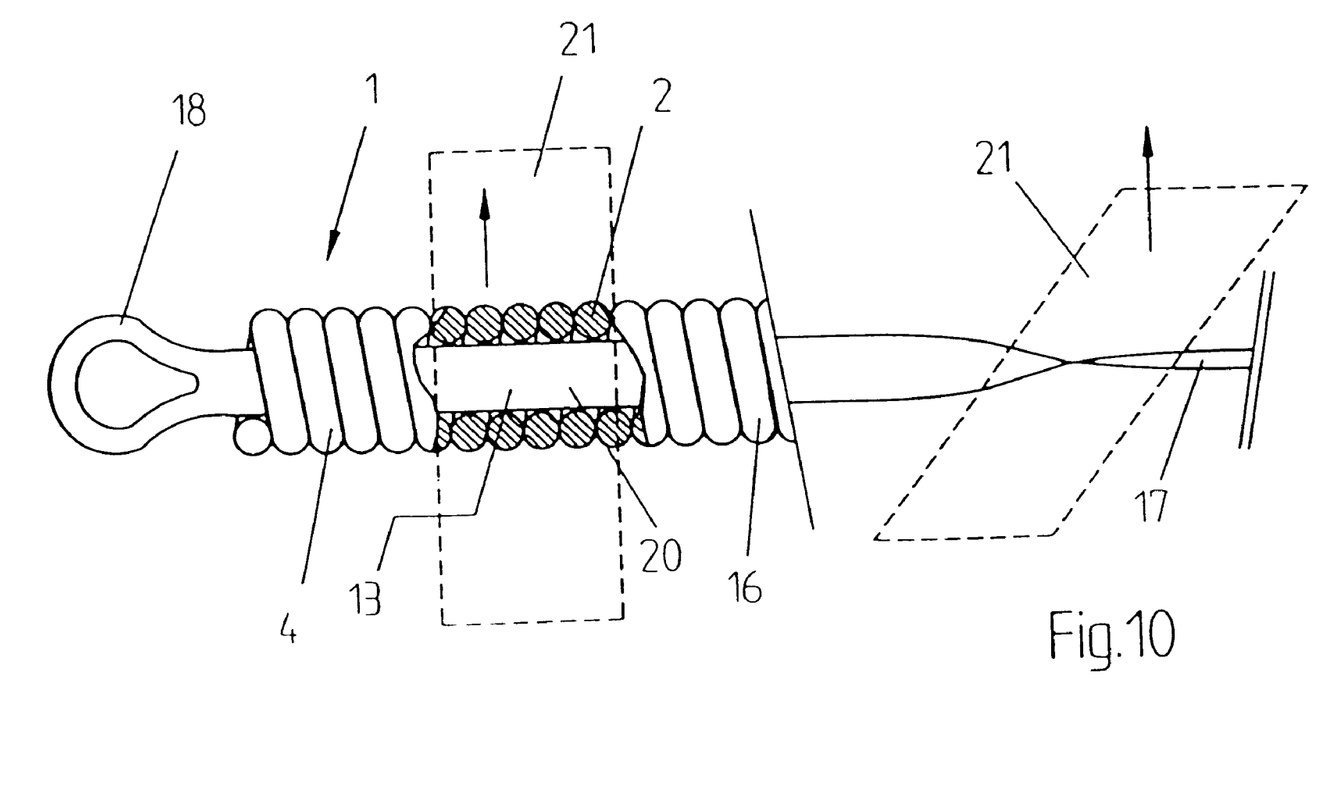
FIG. 10 shows a side view of a further embodiment of the implant according to the invention, with a twisted flat wire as core, in which figure, for the purpose of improved clarity, the primary coil is in part shown in cross-section and is in part omitted.

As will be seen from FIG. 10, a primary coil 2, which has areas of different transverse spring rate along its longitudinal extent, can be formed by a core 13 in the form of a twisted flat wire 20 which is arranged in the lumen of the primary coil 2. The essential point here is that, upon formation of the secondary structure, in order to form an area of low transverse spring rate the primary coil 2 is bent in a direction perpendicular to a reference plane 21 which extends parallel to the broad side of the flat wire 20, and, to form areas 16 of high transverse spring rate, is bent within the above-defined reference plane 21. In the embodiment represented in FIG. 10, the effect is that the primary coil 2 is always bent in the same direction, while the flat wire 20 is twisted inside the primary coil 2. In this case, it is also advantageous if the flat wire 20 is twisted twice through 90°, no that the implant has areas of higher transverse spring rate at both ends, and an area of lower transverse spring rate in the centre. Alternatively, however, the flat wire 20 may not itself be twisted, in which case the primary coil 2, in order to form the secondary structure, must then also be bent in different directions in areas of different transverse spring rate. In this embodiment too, the proximal end of the core 13 is designed as an eyelet 18.

Figure 11:
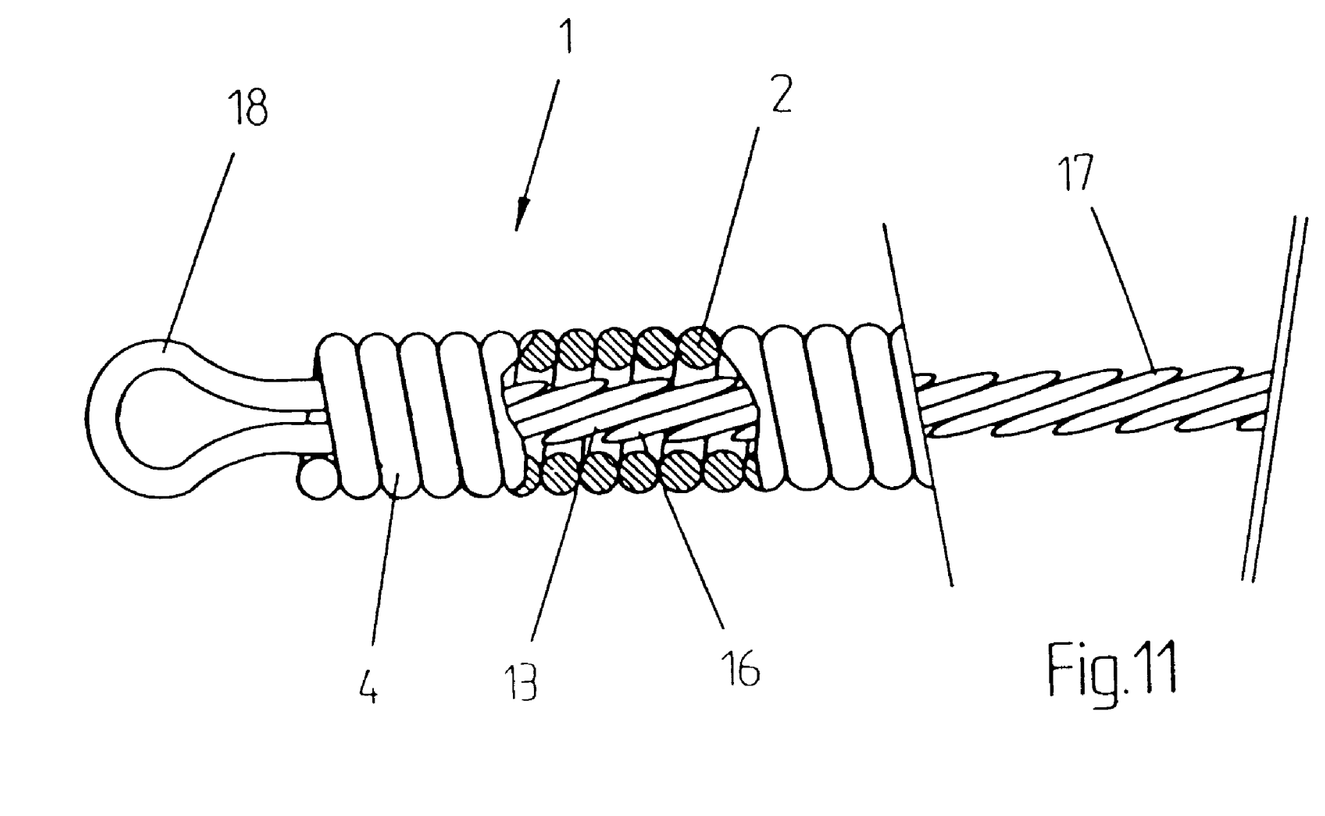
FIG. 11 shows a side view of a further embodiment of the implant according to the invention, with a braid as core, which, along its longitudinal extent, has a variable number of windings of the individual wires per unit of length, in which figure, for the purpose of improved clarity, the primary coil is in part shown in cross-section and is in part omitted.

In the embodiment represented in FIG. 11, the different transverse spring rate of the primary coil 2 along its longitudinal extent is achieved by means of a core 13 in the form of a braid 22 which, in the area 16 of higher bending rigidity, has a lower number of windings of the individual wires per unit of length of the braid 22, and which, in the areas 17 of lower bending rigidity, has a higher number of windings of the individual wires per unit of length of the braid 22. An eyelet 18 is once again provided here at the proximal end of the core 13 as positioning device.

Figure 12:
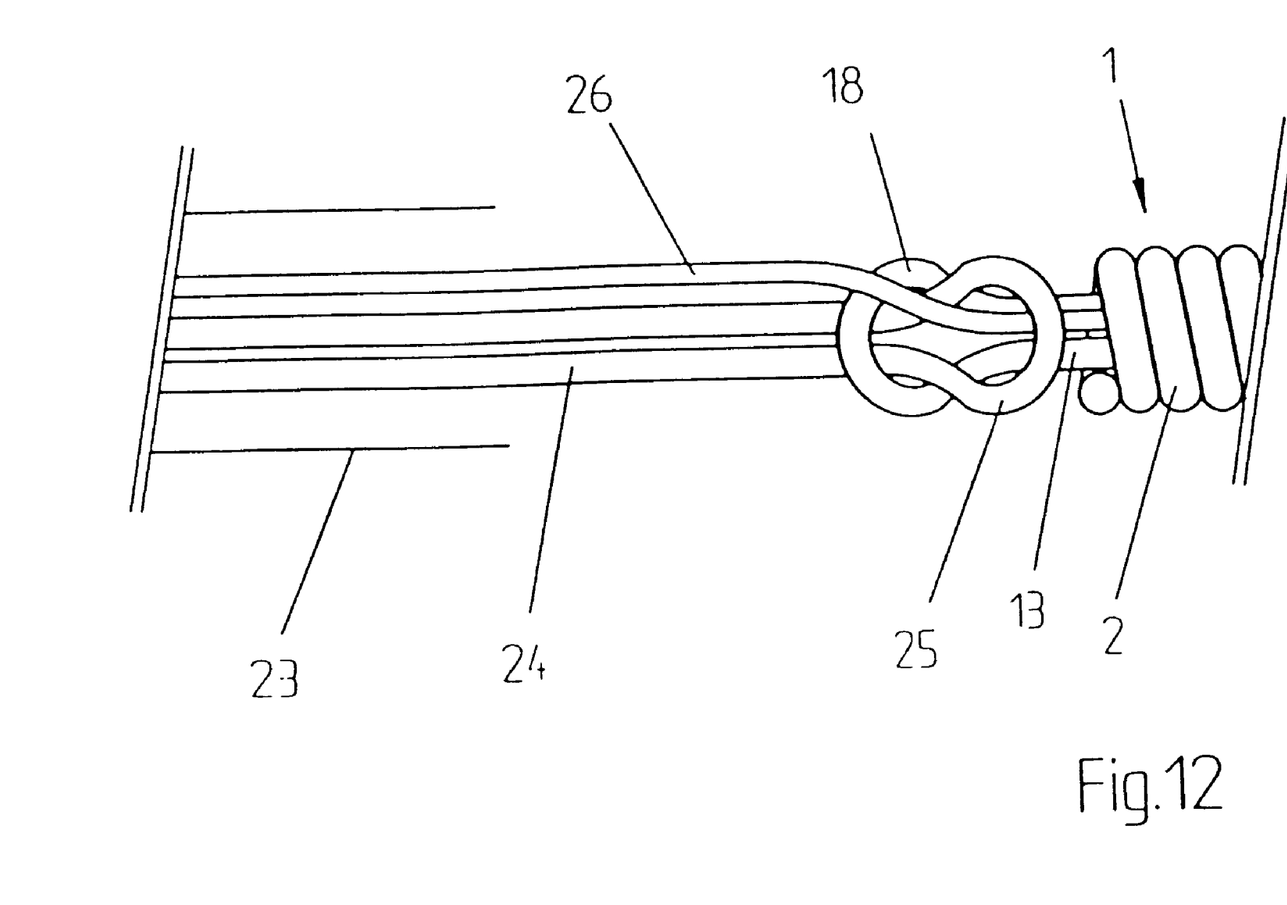
FIG. 12 shows a side view of a set according to the invention, with a catheter, an implant and a positioning wire, where, for the purpose of improved clarity, the catheter is shown in cross-section.

FIG. 12 shows a set for positioning the implants 1 according to the invention, which set includes the implant 1, an insertion catheter 23, a positioning wire 24, and a locking wire 26. The positioning wire 24 is designed in the form of a loop 25 at its distal end. According to the embodiment represented in FIG. 12, the loop 25 of the positioning wire 24 is guided through the eyelet 18 of the implant 11. A locking wire 26 is guided through the loop 25 of the positioning wire 24 in order to secure the latter against being pulled out from the eyelet 18. Of course, this can also be achieved by the eyelet being guided into the loop and secured against being pulled out from the loop by means of a securing wire which is guided through the eyelet.

For positioning the implant 1, the secondary structure is stretched out by pulling the positioning wire 24 and thus the implant 1 back into the insertion catheter 23. Then the whole set is guided into the human or animal body in a manner which is customary and known to the operating surgeon, and the distal end of the insertion catheter 23 is advanced as far as the location for detachment of the implant. The implant 1 is then pushed out of the catheter 23 with the aid of the positioning wire 24 until the implant 1 has emerged completely from the insertion catheter 23 and has assumed its secondary structure 3. A check is then made in a customary manner, for example by radiography, to determine whether the implant 1 has been positioned at the intended location. If this is not the case, the implant 1, because it is still connected to the positioning wire 24, can be pulled into the catheter again and thus repositioned. When the implant 1 is situated at the intended location, the locking wire 26 is pulled back, as a result of which the loop 25 of the positioning wire 24 can separate, and the implant 1 can be finally detached.

From the above description and representation of illustrative embodiments, it will be clear that the invention is not limited to the feature combinations cited in the claims or the description, and that other combinations of the cited features are also conceivable within the scope of the invention.

What is claimed is:

1. An implant for closing passages in organs and defects, comprising:

a primary structure of a resilient material having a predetermined adapted shape with areas of different transverse spring rate along the primary structure's length, wherein the implant, in an operational state, forms a secondary structure of greater diameter than that of the primary structure, wherein the implant is convertible by a guide element from a shape of the secondary structure into a transporting state in which the implant adopts an elongate shape, wherein the implant once again assumes the operational state by removal of the guide element, and wherein the secondary structure has areas with greater radii of curvature where the primary structure has a greater transverse spring rate and areas with smaller radii of curvature where the primary structure has a lesser transverse spring rate.

2. The implant according to claim 1, wherein the primary structure is a primary coil and the primary coil includes a first end section at a first end of said primary coil and a second end section at a second end of said primary coil opposite said first end.

3. The implant according to claim 2, wherein the primary coil includes, on one or more parts of its length, one or more further primary coils, which are combined with the first primary coil in order to increase the spring rate of that part of the primary coil having the further primary coil.

4. The implant according to claim 3, wherein one or more end sections of the primary coil includes, on one or more parts of its length, one or more further primary coils said one or more further primary coils being combined with an end section of said primary coil selected from the group consisting of said first end section, said second end section and combinations thereof.

5. The implant according to claim 3, wherein both end sections of the primary coil include, on one or more parts of their lengths, one or more further primary coils.

6. The implant according to claim 3, wherein said end section of the primary coil includes one or more further primary coils, which further primary coils likewise have, on one or more parts of the length of the further primary coil, one or more additional primary coils.

7. The implant according to claim 6, wherein one or more further primary coils and one or more additional primary coils have substantially the same external dimensions as the primary coil.

8. The implant according to claim 6, wherein one or more further primary coils and one or more additional primary coils are wound between the turns of the primary coil.

9. The implant according to claim 3, wherein both end sections of the primary coil include one or more further primary coils, which further primary coils likewise have, on one or more parts of the length of the further primary coils, one or more additional primary coils.

10. The implant according to claim 3, further comprising a guide element for inserting said implant into a patient wherein turns of the primary coil and of the one or more further primary coils when present are stretched out in the area of a proximal end section of said implant over said guide element wherein said primary coil and said further primary coil are configured in a manner that allows them to be stripped off of said guide element for intersection of the implant in the patent and removal of the guide wire.

11. The implant according to claim 3, wherein the primary coil and one or more further primary coils have a cross section selected from the group consisting of a noncircular, tapered or reduced cross-section in the area of a proximal end section of said implant.

12. The implant according to claim 11, wherein the primary coil and one or more further primary coils have a substantially polygonal cross-section in the area of the proximal end section.

13. The implant according to claim 11, wherein the primary coil and one or more further primary coils have a substantially triangular cross-section in the area of the proximal end section.

14. The implant according to claim 3, wherein one or more further primary coils has a reduced diameter compared to the primary coil.

15. The implant according to claim 1, wherein the primary structure has at least one additional body by means of which the different transverse spring rate is achieved.

16. The implant according to claim 1, wherein the primary structure has a lumen, with a core located in the lumen, which core has areas of different bending rigidity, at least relative to a plane of reference passing through the core lengthwise, along its longitudinal extent.

17. The implant according to claim 16, wherein the core contains two or more wires, the number of wires in areas of greater bending rigidity being greater than in areas of lower bending rigidity.

18. The implant according to claim 16, wherein the core contains at least one wire extending through the entire length of the primary structure, where such wire has a changing diameter, with a greater diameter in areas of greater bending rigidity, and a smaller diameter in areas of lower bending rigidity.

19. The implant according to claim 16, wherein the core contains at least one wire extending through the entire length of the primary structure, where such wire has a circular cross-sectional area in areas of lower bending rigidity, and a polygonal cross-sectional area in areas of greater bending rigidity.

20. The implant according to claim 19, wherein the polygonal cross-sectional surface area is triangular, rectangular or square.

21. The implant according to claim 19, wherein the core contains at least one flat wire.

22. The implant according to claim 21, wherein the flat wire is arranged inside the primary structure such that, upon formation of the secondary structure of the implant, the flat wire, in areas of the secondary structure having smaller radii of curvature, is bent out from a plane which extends parallel to a broad side of the flat wire, and, in areas of the secondary structure having by comparison greater radii of curvature, is bent within this plane.

23. The implant according to claim 16, wherein the core contains a braid of wires, which braid has areas with a different number of windings of the individual wires per unit of length of the braid.

24. The implant according to claim 16, wherein the implant has, at a proximal end, a positioning device which is arranged on the primary structure or on the core and is configured as an eyelet.

25. The implant according to claim 1, wherein the primary structure or the core or both include a memory metal.

26. The implant according to claim 1, wherein by twisting the primary structure, the secondary structure assumes the shape of a cylinder, a cone, a double cone with greater radii at the ends, a double cone with different radii at the ends, a cylinder in which turns of the secondary structure with different radii alternate with each other, two spirals connected by a cylindrical section, a double rosette, a double cone where the turns of the second cone are wound onto the turns of the first cone, or assumes the shape of a plurality of horizontal eight shapes.

27. A set containing an implant according to claim 1, and an insertion device for the implant with an insertion catheter and a guide element, configured to be releasably connected to the implant and movable inside the insertion catheter.

28. The set according to claim 27, wherein the guide element is a positioning device which can be attached to the primary structure or the core of the primary structure in a manner that allows detachment once the implant is properly positioned.

29. The set according to claim 28, wherein in a transportation state, the guide element is releasably connected to the implant, the implant in the elongate state is received completely in the catheter, and the implant is movable inside the catheter by the guide element guided through the catheter.

30. The set according to claim 28, wherein the primary structure of the implant includes an extended proximal end section configured to be fixed on the guide element by increased friction between the implant and the guide element and to be stripped off by compressing the extended windings of the proximal end section together in the axis of the primary coil in order to increase its inner diameter, thereby reducing friction with the guide element and allowing the proximal end section of the implant to be pushed over the widened portion or portions of the guide element.

31. The set according to claim 27, wherein in an area of its distal end, the guide element has a widened portion on one part of its length, in an axis transverse to a longitudinal axis of the guide element.

32. The set according to claim 31, wherein in the area of its distal end, the guide element has at least one further widened portion on one part of its length, in an axis transverse to the longitudinal axis of the guide element and approximately transverse to the first widened portion.

33. The set according to claim 31, wherein the widened portion is about 1.15 times a diameter of the guide element outside the areas of the widened portions.

34. The set according to claim 27, wherein the implant includes a positioning device and the guide element is a positioning wire, which has a hook which engages in the positioning device of the implant.

35. The set according to claim 27, wherein the implant includes a positioning device and the guide element is a positioning wire, which is doubled back inside the catheter and thus forms a loop which engages in the positioning device of the implant.

36. The set according to claim 27, wherein the implant includes a positioning device and the positioning device of the implant is an eyelet, and the guide element is a positioning wire which has a loop which is interlaced with the eyelet and is secured against separation from the eyelet by a locking wire.

\* \* \* \* \*

UNITED STATES PATENT AND TRADEMARK OFFICE
CERTIFICATE OF CORRECTION

PATENT NO. : 6,338,736 B1
DATED : January 15, 2002
INVENTOR(S) : Christoph Boosfeld and Franz Freudenthal It is certified that error appears in the above-identified patent and that said Letters Patent is hereby corrected as shown below:

Column 6,
Line 60, delete "6".

Column 11,
Line 34, delete "30".
Line 44, delete "2", insert -- 2 -- (not bold).

Column 12,
Line 18, delete "no", insert -- so --.

Column 14,
Line 7, delete "patent", insert -- patient --.

Signed and Sealed this

Ninth Day of September, 2003

JAMES E. ROGAN
*Director of the United States Patent and Trademark Office*